United States Patent
Stopp et al.

(10) Patent No.: US 9,833,215 B2
(45) Date of Patent: Dec. 5, 2017

(54) METHOD, DEVICE, AND COMPUTER PROGRAM PRODUCT FOR CAPTURING PROJECTION IMAGES WITH OPTIMIZED MOVEMENT PATH

(71) Applicants: Fraunhofer-Gesellschaft zur Foerderung der angewandten Forschung e.V., Munich (DE); Charite—Universitätsmedizin Berlin, Berlin (DE)

(72) Inventors: Fabian Stopp, Neuenhagen (DE); Marc Käseberg, Biesenthal (DE); Sebastian Engel, Münster (DE); Erwin Keeve, Potsdam (DE); Felix Fehlhaber, Berlin (DE); Eckart Uhlmann, Kiebitzreihe (DE)

(73) Assignees: Fraunhofer-Gesellschaft zur Förderung der angewandten Forschung e.V, München (DE); Charite—Universitätsmedizin Berlin, Berlin (DE)

( * ) Notice: Subject to any disclaimer, the term of this patent is extended or adjusted under 35 U.S.C. 154(b) by 138 days.

(21) Appl. No.: 14/431,286

(22) PCT Filed: Sep. 25, 2013

(86) PCT No.: PCT/EP2013/069928
§ 371 (c)(1),
(2) Date: Mar. 25, 2015

(87) PCT Pub. No.: WO2014/048965
PCT Pub. Date: Apr. 3, 2014

(65) Prior Publication Data
US 2015/0265231 A1    Sep. 24, 2015

(30) Foreign Application Priority Data
Sep. 26, 2012 (DE) .......................... 10 2012 217 460

(51) Int. Cl.
*A61N 5/10* (2006.01)
*A61B 6/03* (2006.01)
(Continued)

(52) U.S. Cl.
CPC ............ *A61B 6/588* (2013.01); *A61B 6/4429* (2013.01); *A61B 6/589* (2013.01); *A61N 5/01* (2013.01);
(Continued)

(58) Field of Classification Search
CPC .. A61B 6/00; A61B 6/027; A61B 6/03; A61B 6/032; A61B 6/035; A61B 6/40;
(Continued)

(56) References Cited

U.S. PATENT DOCUMENTS

| 4,663,726 A | 5/1987 | Chand et al. |
| 6,504,892 B1 | 1/2003 | Ning |

(Continued)

FOREIGN PATENT DOCUMENTS

| DE | 102008046348 A1 | 3/2010 |
| DE | 102010018627 A1 | 10/2011 |

(Continued)

OTHER PUBLICATIONS

International Preliminary Examination Report issued in PCT/EP2013/069928, dated Mar. 31, 2015, 7 pages.
(Continued)

*Primary Examiner* — Anastasia Midkiff
(74) *Attorney, Agent, or Firm* — Faegre Baker Daniels LLP

(57) ABSTRACT

A method, device, and computer program product for capturing projection images of an object are provided. An x-ray beam source is moved by a control unit on a path into a plurality of positions, in which an x-ray beam is transmitted. An x-ray beam detector is moved by the control unit into a (Continued)

plurality of positions, in which the x-ray beam, penetrating the object, is detected. The x-ray beam source and/or the x-ray beam detector are moved on a calculated path around the object, at a constant distance between the x-ray beam source and the x-ray beam detector or the object. The path is described by an nth degree polynomial and determined by the control unit through an optimization of a path along the central x-ray beam. The polynomial is selected such that a safety clearance with respect to the object is maintained and a distance between the x-ray beam detector and the object is minimized.

10 Claims, 11 Drawing Sheets

(51) Int. Cl.
*A61N 5/01* (2006.01)
*A61B 6/00* (2006.01)
*A61B 6/02* (2006.01)

(52) U.S. Cl.
CPC ............... *A61B 6/02* (2013.01); *A61B 6/035* (2013.01); *A61B 6/4085* (2013.01); *A61B 6/4452* (2013.01); *A61B 6/4458* (2013.01); *A61B 2560/0266* (2013.01)

(58) Field of Classification Search
CPC ....... A61B 6/4064; A61B 6/4085; A61B 6/42; A61B 6/44; A61B 6/4429; A61B 6/54; A61B 6/58; A61B 6/588; A61B 6/59; A61B 5/0062; A61B 5/0073; A61B 5/6844; A61B 2576/00; A61B 2560/00; A61B 2560/02; A61B 2560/0266; A61B 2560/04; H05G 1/00; H05G 1/02; H05G 1/26; H05G 1/30; H05G 1/60; G01N 23/00; G01N 23/02; G01N 23/04; G01N 23/06; G01N 23/08; G01N 23/083; A61N 5/00; A61N 5/01; A61N 5/10; A61N 5/1077; A61N 5/1081
See application file for complete search history.

(56) References Cited

U.S. PATENT DOCUMENTS

| | | | |
|---|---|---|---|
| 7,342,992 B2 | 3/2008 | Schomberg | |
| 7,394,923 B2* | 7/2008 | Zou | G01N 23/046 378/4 |
| 7,564,949 B2* | 7/2009 | Sattler | A61B 6/102 378/117 |
| 7,837,385 B2* | 11/2010 | Klingenbeck-Regn | A61B 6/102 378/197 |
| 2004/0066884 A1* | 4/2004 | Claus | A61B 6/025 378/27 |
| 2006/0065839 A1* | 3/2006 | Wagenaar | G01T 1/166 250/363.05 |
| 2007/0189437 A1* | 8/2007 | Yang | A61B 6/032 378/4 |
| 2010/0061509 A1* | 3/2010 | D'Ambrosio | A61B 6/10 378/62 |
| 2012/0035470 A1* | 2/2012 | Kuduvalli | A61B 6/00 600/427 |
| 2012/0224664 A1 | 9/2012 | Maack | |

FOREIGN PATENT DOCUMENTS

| | | |
|---|---|---|
| DE | 102012005899 A1 | 9/2013 |
| WO | 2007130433 A2 | 11/2007 |
| WO | 2014048965 A1 | 4/2014 |

OTHER PUBLICATIONS

International Search Report and Written Opinion issued in PCT/EP2013/069928, dated Nov. 27, 2013, 18 pages.

* cited by examiner

METHOD, DEVICE, AND COMPUTER PROGRAM PRODUCT FOR CAPTURING PROJECTION IMAGES WITH OPTIMIZED MOVEMENT PATH

CROSS-REFERENCE TO RELATED APPLICATIONS

This application is a national phase application of PCT Application No. PCT/EP2013/069928, internationally filed Sep. 25, 2013, which claims priority to German Application No. 10 2012 217 490.7, filed Sep. 26, 2012, both of which are herein incorporated by reference in their entirety.

TECHNICAL FIELD

The present disclosure relates to capturing projection images and, in particular, to a method, device, and computer program product for capturing projection images with an optimised movement path.

BACKGROUND

Different imaging methods are used for the three-dimensional representation of individual objects, such as individual body regions for example. One possible method is cone-beam volume tomography, with which individual, two-dimensional X-ray projections of the body region to be imaged are recorded from different directions and a computation of a three-dimensional representation is subsequently effected. An X-ray source and an X-ray detector move around the object to be imaged, for picture recording. A picture recording path of the X-ray source and the X-ray detector around the object to be imaged, for example a patient, and which is hereby applied, essentially determines the achievable, three-dimensional picture quality of cone-beam volume tomography.

A so-called completeness condition was formulated by Heang K. Tuy (H. Tuy, "An inversion formula for cone-beam reconstruction", SIAM Journal of Applied Mathematics vol. 43, no. 3, pp. 546-552, 1983.), for an exact reconstruction of a volume region. This states that a volume can be reconstructed in an exact manner if all planes which run through the volume also intersect the picture recording path or movement path of the X-ray source at least once. Such a movement path however is difficult to implement, above all with an intra-operative application of cone-beam volume tomography in the operating theatre. In this case, a guarantee of sterility and a free access to the patient are necessary, apart from a high three-dimensional picture quality, i.e. the patient, as the object to imaged, should not be completely enclosed by a device which is used for imaging or by the picture recording path.

Apparatus known from the state of the art use a circular movement of the X-ray detector and of the X-ray source around the patient with an additional linear forwards movement (so that e.g. a spiral path results) or with an additional inclination. Such a device is e.g. known from the patent document U.S. Pat. No. 6,504,892 B1. A further possibility is to provide a simple circular path or orbit around the patient, with which the patient, although not being completely enclosed, the reconstruction of the scanned volume exclusively in a central plane is however complete. The volume outside this central plane cannot be reconstructed in an exact manner. Further solution possibilities comprise saddle-like movement paths which are also called sweep/wobble trajectories, or also the use of several individual orbits of the X-ray source about the target region, e.g. two circular paths running parallel to one another.

SUMMARY

This disclosure provides a method and a device, with which the mentioned disadvantages are avoided, with which a high three-dimensional picture quality with a free access to the object to be imaged is achieved.

The described method, the described device and/or the described computer program product can be applied in medical applications, such as with intra-operative applications, for example with cone-beam volume tomography. Medical fields of application include accident surgery, oral surgery, orthodontics, facial surgery, orthopaedics, neurology, urology, cardiology or emergency scans in the case of a polytrauma.

BRIEF DESCRIPTION OF THE DRAWINGS

Embodiments of the disclosure are represented in the drawings and are hereinafter explained by way of the FIGS. 1-12.

There are shown in.

DETAILED DESCRIPTION

Figure 1:
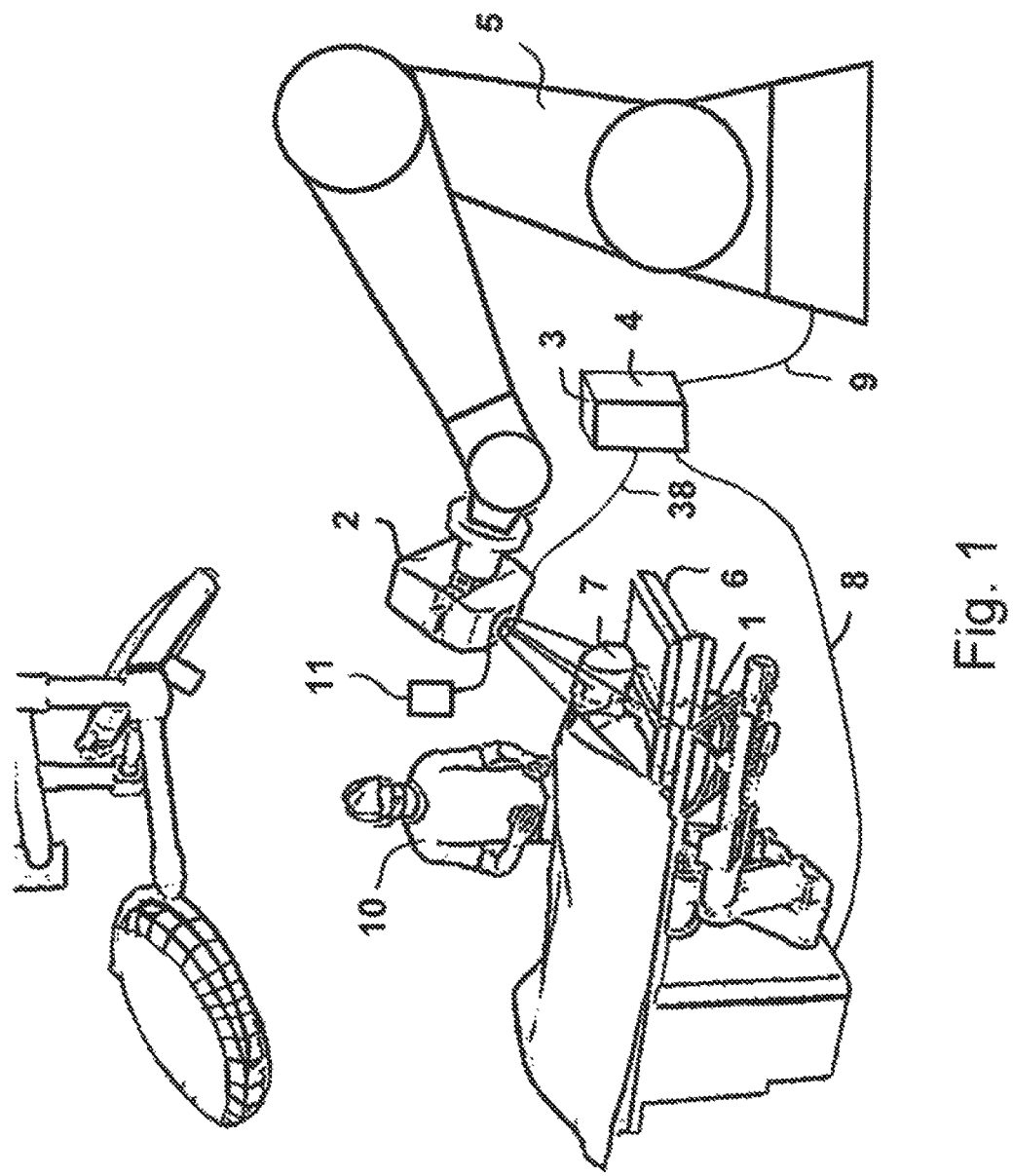
FIG. 1 a perspective view of a device for recording X-ray pictures, according to embodiments described in the disclosure.

A method according to the disclosure for recording projection pictures of an object to be imaged makes use of an imaging device which comprises a beam source, a beam detector and a control unit. The beam source by way of the control unit is moved on a path into several positions, in which a beam departing from the beam source in a cone-beam-like manner around a central beam is emitted in each case, wherein on moving the beam source, the beam detector is likewise moved by the control unit into several positions, in which in each case the beam departing from the beam source and penetrating the object to be imaged is captured for recording the projection picture. The beam source and/or the beam detector are moved in each case about the object to be imaged, on a path which is described by a polynomial of nth degree, computed by the control unit by way of an optimisation of a predefined path and has a constant distance between the beam source and the beam detector, determined along a central beam, and/or a constant distance between the beam source and the object to be imaged, determined along the central beam. Hereby, the polynomial in each case is selected in a manner such that a safety distance to the object to be imaged is kept and simultaneously a distance between the beam detector and the object to be imaged is minimised. A polynomial of the "nth" degree is thereby to be understood as any integer polynomial, thus "n" a natural number.

On account of the polynomial movement path of the beam detector, this during a picture recording is closer to the object to be imaged than with methods applied until now, by which means the volume which can be imaged on the projection pictures is enlarged. The polynomial path is hereby computed by the control unit. The completeness condition of Tuy is fulfilled by way of this method, at least for a target volume in the centre of the path and thus a qualitatively good, exact, three-dimensional reconstruction of the object to be imaged can be effected in a further step. The use of the polynomial movement path permits an optimisation of the movement path in a wide range, whilst taking the conditions of the surroundings into account. A computation of the movement path is simplified, and the maintenance of the safety distance is simultaneously ensured by way of the constant distance between the beam source and the object to be imaged or between the beam source and the beam detector. A volume region which fulfils the completeness condition is larger with the method suggested here, compared to the known methods from the state of the art, so that a larger volume can also be reconstructed in an exact manner. The safety distance which is to be maintained between the beam detector and/or the beam source and the object to be imaged can be constant for the complete movement, but alternatively can also have a previously defined value for each point of the movement, wherein this value is differently large for different points. Thus a defined distance can always be maintained and collisions avoided. A minimisation of the distance between the beam detector and the object to be imaged is to be understood in that the distance lies as close as possible to the safety distance, thus an as small as possible distance between the beam detector and the object is present.

In some embodiments, the displacement of the beam source and the displacement of the beam detector are effected simultaneously. In some embodiments, the beam source and the beam detector are moved in a temporally staggered manner. The simultaneous displacement permits a quick implementation of the method, whereas a moving of the apparatus one after the other provides the possibility of still being able to carry out modifications on the object to be imaged, with which one of the apparatus in the aimed end condition would render an access more difficult.

The object to be imaged can be placed on a rest surface for the improved and secure holding, wherein in this case a safety distance to the rest surface is maintained additionally or alternatively to the safety distance to the object to be imaged, by way of the polynomial path. In some embodiments, the rest surface is a table and, in some embodiments, a table in an operating theatre, but it can also encompass a further equipping of the operating theatre.

In some embodiments, the polynomial movement path describes a movement path with respect to a centre of a picture plane of the beam detector. A condition for the setting of the safety distance thereby can be that the beam detector and/or the beam source, such as a surface of a housing of the mentioned apparatus, is distanced, in some embodiments at least 80 mm, in some embodiments at least 100 mm, and in some embodiments at least 120 mm from the object to be imaged and/or the rest surface, at each position of the movement path of the beam source. The safety distance can of course also be selected smaller than 80 mm.

A further condition can lie in a maximal distance between the beam source and/or the beam detector and the object to be imaged and/or a possible working region taking kinematics of the beam source and/or of the beam detector into account, i.e. this maximal distance not being permitted to be exceeded on moving the beam source or the beam detector.

The distances in each case can be measured from a middle point of the respective object to a further middle point of another object, from a surface of the object to a further surface of a further object or from the middle point of the object to the further surface of the further object.

The polynomial in each case can be defined by at least two grid points, which can be specified externally or specified, and determined by way of an optimisation whilst taking into account the grid points and/or by way of an optimisation of a predefined circular path. On optimising several paths, each of the polynomials or also only a single one can be optimised by way of at least two grid points in the previously described manner. The optimisation can thereby be effected in a direct manner by way of the already described conditions and/or via the predefined grid points with a subsequent checking of a polynomial course.

Polynomials with exclusively even powers or polynomials with exclusively odd powers can be used as polynomials. Of course, polynomials with even as well as odd powers are also possible. Thus an optimisation of the polynomial path can be simplified according to the application purpose.

An origin of a reference coordinate system, in which the movement path is fixed and optimised, can be located in the middle point of the object to be imaged or centrally on the rest surface. A fixed point which is simple to determine can be set by way of this, for the simplified computation.

In as much as one assumes a circular path with the movement path of the beam source, this circular path can be optimised by way of the polynomial by way of the already described conditions. Instead of a circular path, a path of path-pieces which are linear in sections can also be approximated and/or optimised via the polynomial of the nth degree and thus form the computed path, on which the beam source or the beam detector are displaced.

In some embodiments, the beam source and the beam detector are guided in a manner lying opposite one another and the central beam hits the beam detector in an orthogonal manner. A three-dimensional reconstruction is simplified by way of this. In some embodiments, the central beam does not hit the beam detector orthogonally, but at an angle different from 90°. The movement of the beam source can be effected separately from the movement of the beam detector, in order to ensure an as free as possible setting of the movements.

In some embodiments, the maximal height of the path of the beam detector is determined by a maximal opening angle of the path of the beam source which is determined starting from the middle point of the object to be imaged. The maximal height can be used for setting a starting point, an end point and/or a reversal point of the path of the beam source and/or of the path of the beam detector. Thus individual points of the movement path are defined at least up to a certain degree by way of specifications inherent of the construction type. The starting point and the end point of the path of the beam detector preferably lie opposite the starting point and the end point of the path of the beam source along the central beam running through the middle point of the object to be imaged. The opening angle hereby describes the angle which runs between two beams which lie in a plane and which, departing from the middle point of the object to be imaged, as a common initial point, run to the starting point and to the end point of the path of the beam detector. In some embodiments, the reversal point of the path of the beam detector lies opposite the reversal point of the path of the beam source. A geometrically particularly simple form of an assignment is selected by way of this.

The maximal height departing from the middle point of the object to be imaged as a scanning centre with respect to the rest surface or with respect to the reference coordinate system can be determined by way of two methods.

In a first method, the maximal height of the detector is set as end positions by way of a possible or necessary working region of the kinematics of the beam detector. Subsequently, the maximal opening angle of the path of the beam source is determined whilst taking into account the position of the scanning centre, by way of this height, in some embodiments maximally 250 mm, and in some embodiments maximally 150 mm, above the middle point of the object to be imaged or of an edge of the rest. The lower the height of the scanning centre and the higher the end positions of the beam detector, the larger is the maximal opening angle.

A maximal opening angle which is to be applied is defined in a second method. Intersection points of the central beam of the beam source departing from the starting point and the end point of the path of the beam source are subsequently determined. These two intersection points define necessary maximal positions of the middle point of the detector and thus the necessary height of the path of the detector. Restrictions which simplify the optimisation can be defined by way of the mentioned methods.

The movement of the beam source and/or of the beam detector can be open, i.e. be effected on an open path. An open path is hereby to be understood as a path with which the starting point and the end point of the path are different to one another and/or the path does not completely enclose the object to be imaged. A system construction for implementing the picture recording method which does not fully enclose the object to be imaged becomes possible by way of this. Thus an access to the object to be imaged is always ensured. Alternatively, the movement of the beam source and/or of the beam detector can also run on a closed path with which the starting point and the end point correspond to one another.

The movement of the beam source and/or of the beam detector can alternatively or additionally comprise at least one reversal point, at which a direction change takes place. An increased quality of a three-dimensional reconstruction is achieved by way of this. In some embodiments, a first path section up to the reversal point is spatially different from a second path section from the reversal point, so that several different positions can be covered.

In some embodiments, the beam detector and/or the beam source is moved along and/or about at least two axes which can be perpendicular to one another. An activation as well as a later possibly effected evaluation is considerably simplified by way of this simple geometric relation of the axes and thus of the movement. The movements about the two axes can also be of a different type, thus for example comprise a linear movement and a rotation movement.

In some embodiments, an inclination of the beam source is set such that a beamed surface of the beam detector is maximised at a fixed angle of the cone beam. A spatial extension of the cone beam is defined in dependence on the beam source by way of the fixed angle, so that a complete surface of the beam detector is beamed for generating maximal information, by way of the inclination of the beam source.

The control unit can carry out at least one of the movements of the beam source and/or of the beam detector in an automated manner, so that projections pictures are obtained without further human effort. In some embodiments, both movements are carried out by the control unit in an automated manner. Alternatively or additionally, an evaluation unit can compute the three-dimensional reconstruction of the object to be imaged from the projection pictures. In some embodiments, the control unit and the evaluation unit are combined into one apparatus, preferably into a computer.

In some embodiments, the beam source is an X-ray source and an emitted beam is X-ray radiation as well as the beam detector an X-ray detector, preferably an X-ray flat detector.

A device for recording projection pictures comprises a beam detector, a beam source and a control unit, wherein the control unit is configured to move the beam detector and the beam source in each case into several positions and to record a projection picture in each of the positions. The beam source for this is configured to emit a beam (radiation) in a cone-beam-like manner about a central beam, and the beam detector is configured to capture the emitted beam penetrating through the object to be imaged. The control unit for this is designed to move the beam source and the beam detector in each case on a path about the object to be imaged, said path being described by a polynomial of the nth degree and being computed by the control unit by way of optimising a predefined path, wherein the computed path has a constant distance between the beam source and beam detector, said distance determined along a central beam, and/or a constant distance between the beam source and the object to be imaged, said distance determined along the central beam, wherein the polynomial is selected in each case to maintain a safety distance to the object to be imaged and simultaneously to minimise a distance between the beam detector and the object to be imaged. The minimisation can be effected to the safety distance, so that the beam detector lies as close as possible to the object to be imaged. Thus the device serves for the simple recording of quality projection pictures, from which also high-quality three-dimensional reconstructions can be computed.

The device is suitable for carrying out the described method.

The device comprises the evaluation unit with the already described characteristics for computing the three-dimensional reconstructions.

A computer program product comprises a command sequence which controls a device for recording projection pictures, comprising a beam detector, a beam source and a control unit, wherein the control unit is configured to move the beam detector and the beam source in each case into several positions and to a record a projection picture in each of the positions, the beam source is configured to emit a beam in a cone-beam-like manner about a central beam, and the beam detector is configured to detect the emitted radiation, said controlling of the device being such that the beam source and the beam detector in each case are moved on a path about the object to be imaged, said path being described by a polynomial of the nth degree and being computed by the control unit by way of an optimisation of a predefined path, wherein the computed path has a constant distance between the beam source and the beam detector, said distance determined along the central beam, and/or a constant distance between the beam source and the object to be imaged, said distance determined along the central beam. Hereby, the polynomial is selected in a manner so as to maintain a safety distance to the object to be imaged and to simultaneously minimise a distance between the beam detector and the object to be imaged. The minimisation can be effected to the safety distance, so that the beam detector lies as close as possible to the object to be imaged and the distance between the beam detector and the object to be imaged lies as close as possible to the safety distance.

The computer program product is also suitable for carrying out the described method. In some embodiments, the computer program product is applied for the control of the already described device. The implementation of the method and/or the activation of the device by way of the computer program product can be effected when the computer program product runs on a computation unit.

The computer program product can be loaded directly into an internal memory of the computation unit or already stored in this and sometimes comprises parts a program code for carrying out the described method or for activating the described device when the computer program product runs or is carried out in the computation unit. The computer program product can be stored on a machine-readable carrier, preferably a digital memory medium. The computer program product can also comprise a computer program which has software means for carrying out the described method and/or for activating the described device when the computer program is carried out in an automisation system or on the computation unit.

FIG. 1 in a perspective view shows a device for recording X-ray pictures, which are firstly taken as two-dimensional projection pictures and are subsequently processed further into three dimensional pictures. The device for this comprises an X-ray detector 1 as a beam detector, an X-ray source 2 as a beam source, a control unit 3 which together with an evaluation unit 4 controls a robot arm 5, and a table in an operating theatre, thus an operating table 6 as a rest surface for the object to be imaged, which in the example represented in FIG. 1 is a patient 7. In some embodiments, other beam sources and beam detectors can be applied instead of the X-ray source 2 and the X-ray detector 1.

The X-ray detector 1 is a digital X-ray flat detector and is displaceably mounted below the operating table 6 on a guide, but, in other embodiments, it can be connected to the operating table 6 in a positionally fixed manner. The X-ray detector 1 for its movement is guided on five-fold kinematics which can move the X-ray detector 1 in an automated manner. In some embodiments, the X-ray detector 1 and its guiding correspond to the respective components of the German patent application 10 2012 005 899.3. The X-ray detector 1 in particular can also be displaced such that it is located next to the object to be imaged.

The X-ray source 2 emits X-ray radiation in a cone-beam like manner about a central beam. This X-ray radiation penetrates the head of the patient 7 or another part of his body and is detected by the X-ray detector 1. A thus obtained two-dimensional projection recording is transferred via a cable 8 or also in a wireless manner to the evaluation unit 4, which in the represented example is a personal computer, for further processing.

The X-ray source 2 is fastened on the end of the robot arm 5, by which means the X-ray source 2 can be moved in an automated manner. The robot arm 5 is an arm of an industrial robot and is movably mounted on a floor of the operating theatre. In some embodiments, the robot arm 5, the X-ray source 2, the operating table 6 and the X-ray detector 1 shown in FIG. 1 correspond to the respective components in the document DE 10 2010 018 627 A1. The X-ray beamer 2 can be moved in at least four degrees of freedom.

The robot arm 5 is controlled via the control unit 3 and the control signals are either transferred or transmitted to the robot arm either via a cable 9 or in a wireless manner. The control unit 3 for this comprises a computer program product with a command sequence which activates the described device for carrying out the method. The computer program product is stored on a machine-readable carrier such as a hard disk, a CD or a USB stick and comprises parts of a program code which activates the device as described and carries out the described method when the computer program product runs on the control unit 3. The control unit 3 corresponds to the personal computer which also forms the evaluation unit 4 but can also be designed as a separate device.

A user 10 of the device, for example a surgeon or his assistant in the operating theatre, thus intra-operationally, thus during the operation on the patient 7, can view two-dimensional projection pictures which have been taken in different positions of the X-ray source 2 and the X-ray detector 1, as well as three-dimensional images of a target volume imaged from several positions, on a screen 11 which is connected to evaluation unit 4 via the cable 38, said three-dimensional images having been created by the evaluation unit 4. Generated volume data of the target volume of the patient 7 can of course not only be obtained during the surgical operation but also already before this or thereafter, by way of the device represented in FIG. 1 and the description described hereinafter. Medical fields of application include accident surgery, oral surgery, orthodontics, facial surgery, orthopaedics, neurology, urology, cardiology or emergency scans in the case of a polytrauma.

The control unit 3 is designed to move the X-ray source 2 and the X-ray detector 1 each on a path around the patient 7, said path described by a polynomial of the nth degree. For this, the control unit 3 also computes these mentioned paths, usually by way of an optimisation of a defined path. This polynomial of the nth degree can be determined or set in one method step.

Thus a method can be carried out with the device shown in FIG. 1, with which the projection pictures of the patient 7 are taken from several positions. The control unit 3 for this simultaneously moves the X-ray detector 1 and the X-ray source 2 into one of the positions, and the X-ray source 2 emits X-ray radiation in a cone-beam-like manner about a central beam in the direction of the patient 7 and this at least partly penetrates through the patient 7 and is partly absorbed, wherein the X-ray detector 1 detects the non-absorbed components. The X-ray source 2 and the X-ray detector 1 are subsequently moved into a further position by way of the control unit 3, and one of the projection recordings is again taken. The X-ray source 2 and the X-ray detector 1 are each led on a polynomial movement path which in each case is accomplished by an optimisation of a defined path which is subsequently specified in more detail hereinafter, i.e. the movement path of the X-ray source 2 as well as the movement path of the X-ray detector 1 are optimised per se. In some embodiment examples of course also only one of the paths can be polynomially optimised. The X-ray detector 1 and the X-ray source 2 can also be moved one after the other in further embodiments.

Figure 2:
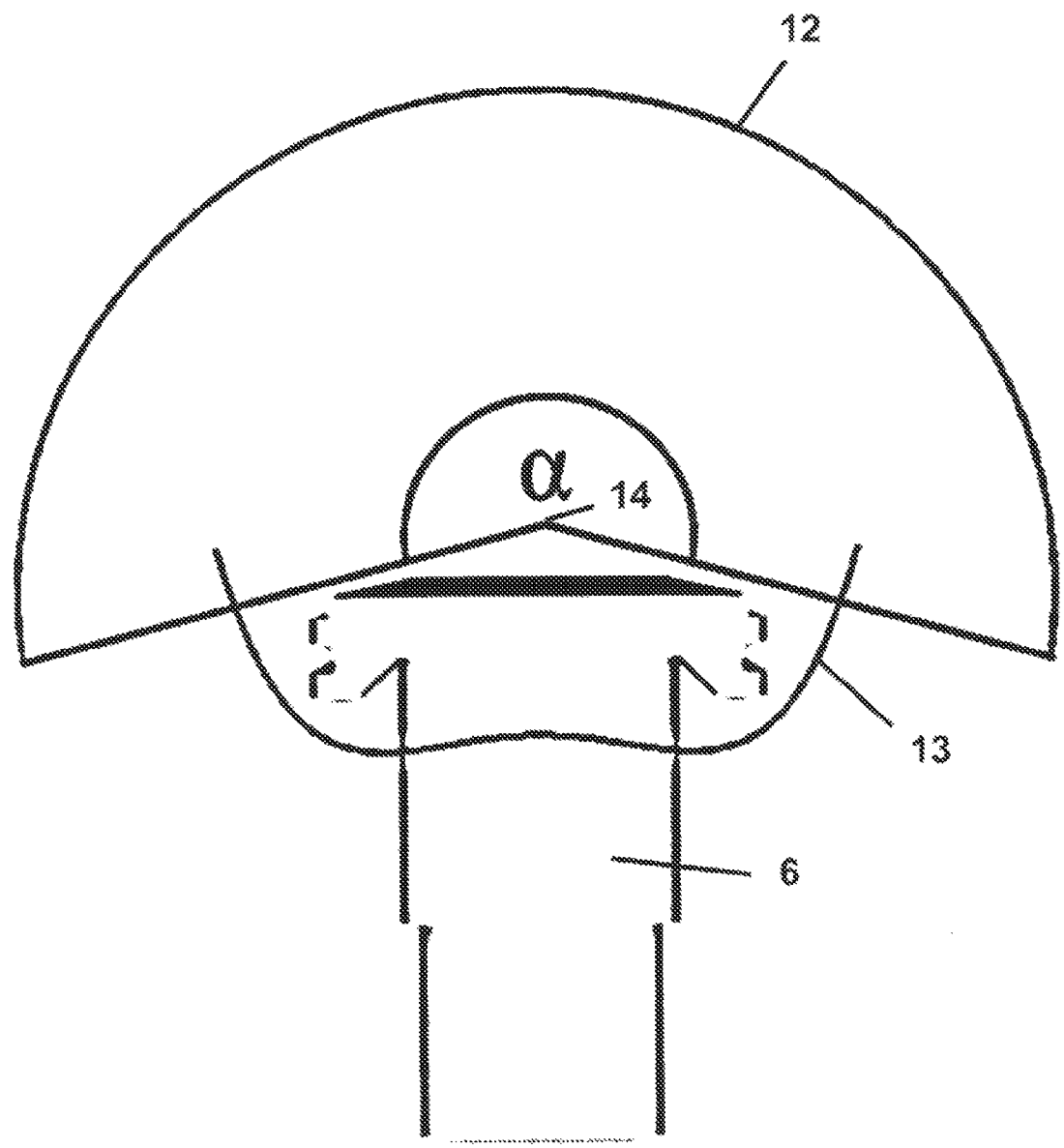
FIG. 2 a sectioned representation of an operating table with a movement path of an X-ray source and with a movement path of an X-ray detector, according to embodiments described in the disclosure.

FIG. 2 in a sectioned representation of the operating table 6 shows a path 12 of the X-ray source 2 which runs chiefly above the operating table 6, and a path 13 of the X-ray detector 1 which mainly runs below the operating table 6. Recurring features are provided with the same reference numerals in these as well as in the following figures. The path 12 of the X-ray source 2 describes an arc with an angle of opening α of 196° which results from an arc of 180° plus a cone beam opening angle of γ of 16°. A middle point of the arc lies in a middle point 14 of the target volume and serves as an origin of a reference coordinate system, so that a distance between this middle point 14 and the X-ray source 2 remains constant during the travel of the path. The path 12 of the X-ray source 2 runs in a plane. The path 13 of the X-ray detector 1 runs in a curved line below the operating table 6 but has two side-pieces which lie next to the operating table 6 and, in as much as a patient 7 lies therein, also next to this patient. The path 13 of the X-ray detector 1 likewise runs in a planar manner in a plane, wherein the plane of this path is identical to the plane 12 of the X-ray source 2. The X-ray detector 1 instead of on the path 13 shown in FIG. 2 can also be led on an arched path around the patient 7, wherein a distance between the X-ray detector 1 and the middle point 14 of the target volume is constant. The origin of the reference coordinate system can however lie centrally on the operating table 6 in further embodiment examples.

Starting from the planar recording path 12 of the X-ray source 2, along which the X-ray source 2 is moved into several positions for recording the projection pictures, the movement path 13 of the X-ray detector 1 can be modified in an optimisation method and be described by a polynomial function of the nth degree. The polynomial path runs around the patient 7 with the target volume and also around the operating table 6. The polynomial is defined in a manner such that on the one hand a safety distance to the operating table 6 or other apparatus of the operating theatre or persons in the operating theatre is ensured, and on the other hand that an a small as possible distance to the object on the operating table 6, thus to the patient 7 is present. This is effected in the same manner for the X-ray beamer 2. The distance between the X-ray source 2 and the X-ray detector 1 in the ideal case is minimised to such an extent that it just about corresponds to the safety distance which is to be maintained between the mentioned devices and the operating table or the patient 7 or other apparatus and persons.

Figure 3:
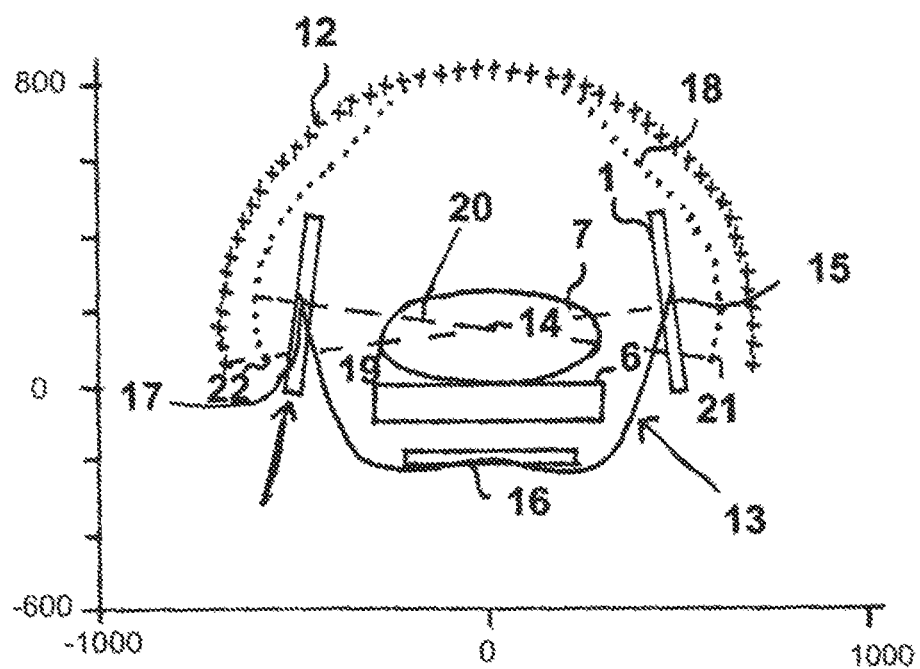
FIG. 3 a view of the movement paths of the X-ray source and of the X-ray detector, which are shown in FIG. 2, in a reference coordinate system, according to embodiments described in the disclosure.

The already adapted path 13 of the X-ray detector 1 as well as the initial path 12 and an adapted polynomial path 18 of the X-ray source 2 through individual ones of the moved-to positions are represented in FIG. 3 in the reference coordinate system. The patient 7 lies on the operating table 6. The middle point 14 of the drawn coordinate system coincides with the middle point of the target volume of the patient 7 as the object to be imaged. As is represented in FIG. 1, the target volume can be the head. The middle or centre point of the target volume can thereby be a geometric middle point as well as a centre of mass. The path 13 of the X-ray detector 1 is already optimised by a computation of the path 13 which is carried out by the control unit 3 and starts with the drawn position 15 of the X-ray detector 1 at the right of the patient 7. The X-ray detector 1 is led along the path 13 via a middle position 16 below the patient 7 into an end position 17 on the left next to the patient 7. The path 13 runs symmetrically to the middle position 16. The original path 12 of the X-ray source 2 before the optimisation is represented by positions in FIG. 3 which are indicated by crosses. The polynomial path 18 which is obtained after the optimisation is characterised by points. The paths 12 and 18 are the same in a middle part above the operating table 6, otherwise the positions of the path 18 lie closer to the operating table 6 than the corresponding positions of the path 12. The evaluation of the polynomial functions can be effected via suitable grid points, in the present example via the positions of the path 18 which coincide with positions of the original path 12, and/or via a direct optimisation of the polynomial movement path, i.e. an optimisation without the specification of grid points, whilst taking into account the specified safety distance to the operating table 6 and to the patient 7. These grid points are specified in a separate method step and are taken into account on computing the path. In some embodiments, the X-ray detector 1 as well as the X-ray source 2 maintains the safety distance to the object to be imaged, wherein the safety distance between the X-ray source and the object to be imaged can be larger, smaller or the same as the safety distance between the X-ray detector and the object to be imaged.

The polynomial which is used for optimisation can comprise only even powers or, only odd powers or both types of powers. An example for an optimised polynomial of the 6th degree as a polynomial resulting from the optimisation for the path 13 of the X-ray detector 1 is $$y = 9.805256 \ast 10^{-15} \ast x^6 + 1.150705 \ast 10^{-8} \ast x^4 - 1.10097 \ast 10^{-3} \ast x^2 - 200$$

Hereby, the grid points for the path 13 of the X-ray detector 1 (0, −200), (−200, −225), (200, −225), (−375, −100) (375, −100), (−475, 250) and (475, 259) were hereby used in the coordinate system drawn in FIG. 3. The origin of the reference coordinate system is thereby located in the middle of a surface of the operating table 6. The safety distance of the X-ray detector 1 in the embodiment example shown in FIG. 3 is 80 mm, but can also be greater or smaller depending on the situation.

A maximal height of the polynomial movement paths 13 and 18 of the X-ray source 2 and of the X-ray detector 1 is determined by the maximal opening angle α and the position of the target volume: The starting point 15 and the end point 17 of the path 13 of the X-ray detector 1 result as intersection points of the central beams 19 and 20 which run through the middle point 14 and which the X-ray source 2 emits in a starting point 22 of the path 18 or the path 12 and an end point 21 of the path 18 or the path 12, with the optimised movement path of the X-ray detector 1.

However, the starting point 15 and the end point 17 can be reduced in height due to a possibly set working region (for example when using the arrangement applied in the German application 10 2012 005 899.3). The maximal opening angle α and the starting point 22 and the end point 21 can be adapted accordingly if necessary. In some embodiments, the maximal opening angle which is to be achieved can also be set and an adaptation be effected assuming such.

Figure 4:
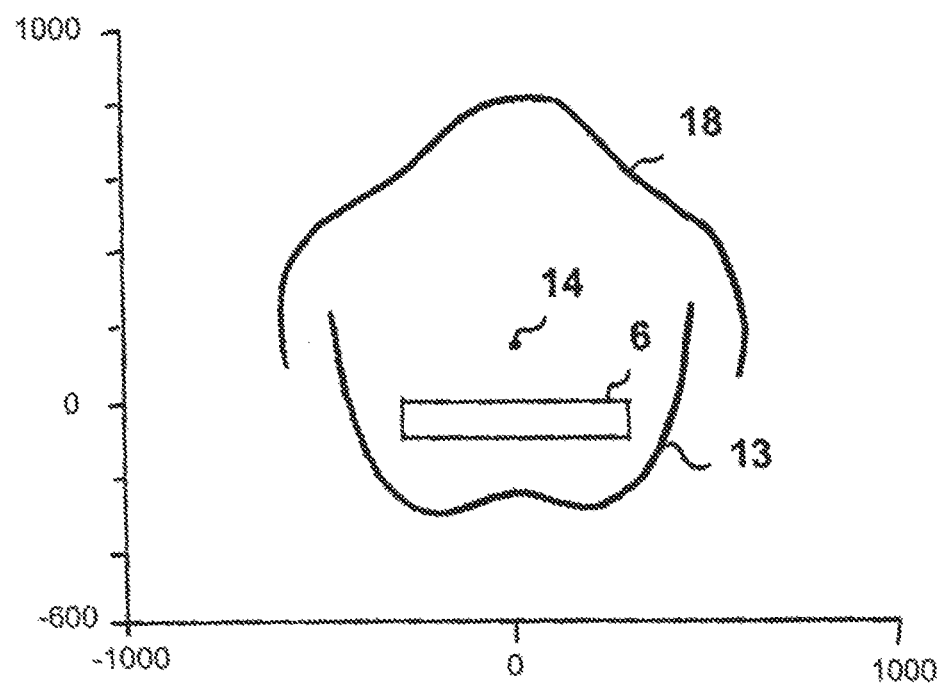
FIG. 4 a representation of the movement paths of the X-ray source and of the X-ray detector, said representation corresponding to FIG. 3, with a constant distance between the X-ray source and the X-ray detector, according to embodiments described in the disclosure.

The path 18 is represented as a continuous path in FIG. 4, in a manner corresponding to the picture 3. A distance of the X-ray source 2 to the middle point 14 was adapted for the optimised polynomial path 18 in a manner such that a distance along the central beam between the X-ray source 2 and the X-ray detector 1 which are always opposite one another in the course of the paths shown in FIG. 4, is always constant. Alternately, in further embodiment examples, a distance between the X-ray source 2 and the middle point 14 or a surface of the target volume can also be constant. In some embodiments, a variable distance of the X-ray source 2 to the X-ray detector 1 or to the middle point 14 or to the surface of the target volume can also be provided, in order to avoid collisions with other apparatus for example. Likewise, an alignment of the X-ray detector 1 can be effected orthogonally to the central beam of the X-ray source 2, as is also represented in FIG. 4. However, in further embodiment examples, the polynomial movement path 13 of the X-ray path detector 1 can run as closely as possible to the patient 7 or to the operating table 6. The distance of the polynomial movement path to the operating table 6 and/or to the patient 7 can be reduced further by way of oblique projection recordings by way of this. The polynomial movement paths 13 and 18 are defined with respect to a centre of a picture plane of the X-ray detector 1.

Figure 5:
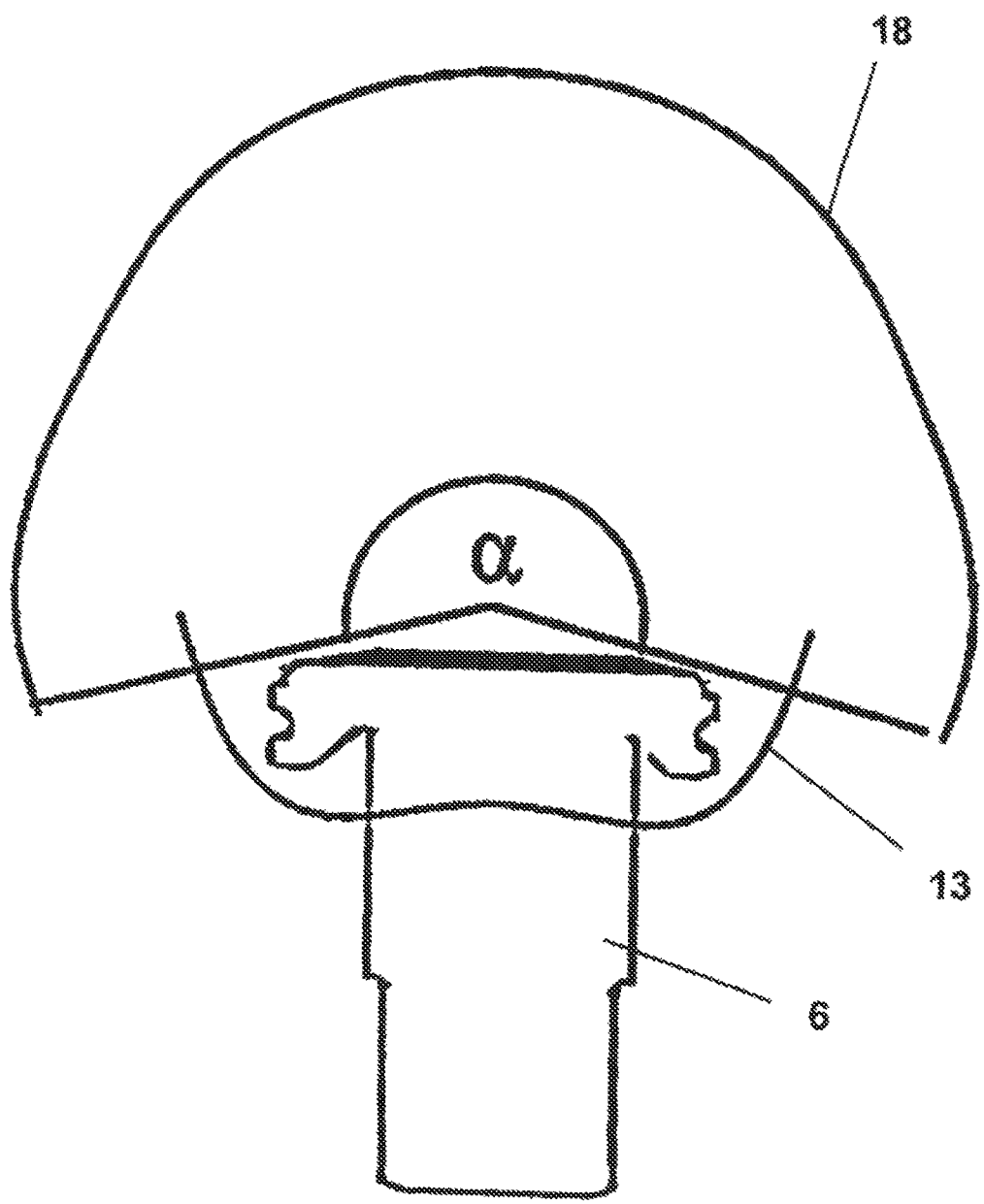
FIG. 5 a representation of the movement paths represented in FIG. 4, in a manner corresponding to FIG. 2, according to embodiments described in the disclosure.

FIG. 5 in a view corresponding to FIG. 2 represents the obtained optimised paths 13 and 18 which are represented in FIG. 4, together with the opening angle $\alpha$.

Figure 6:
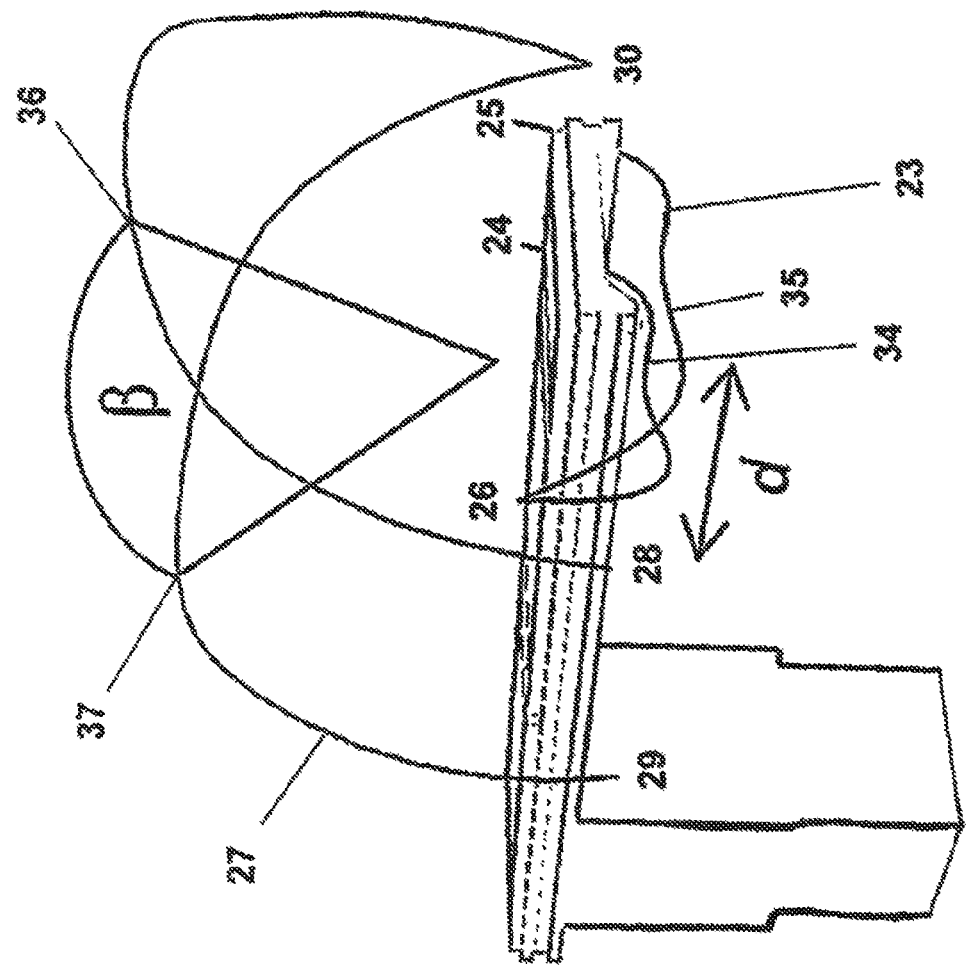
FIG. 6 a perspective representation of the operating table with the movement paths of the X-ray source and the X-ray detector, according to embodiments described in the disclosure.

As shown in FIG. 6 in a perspective view, a displacement d in the longitudinal direction of the operating table 6 can be effected additionally to the lateral deflection of the X-ray detector 1 to the left and right of the operating table 6, also by way of the device described in the German patent application 10 2012 005 899.3 A length of this displacement in FIG. 6 is 300 mm, In some embodiments, the kinematics of the X-ray detector 1 can displace this by maximally 250 mm beyond the table edge of the operating table 6, which also sets the maximal opening angle $\alpha$.

The X-ray detector 1 alternatively or, as in FIG. 6, additionally to this longitudinal displacement, carries out a movement on a path 23, with which a starting point 24 and an end point 25 although lying on the same side of the operating table 6, however lie spatially offset to one another by the amount of the longitudinal displacement. Lying opposite these points 24, 25 is a reversal point 26, at which the X-ray detector 1 on the path 23 undergoes a direction change of the movement. Accordingly, two middle positions 34, 35 of the movement 23, in which positions the X-ray detector 1 is located closest to the target volume and which lie spatially offset to one another also exist. The X-ray detector 1 thus during the picture recording procedure moves on the polynomial path 23 from one side of the patient 7 to the opposite side and back again. The X-ray detector 1 is displaced in the longitudinal direction of the operating table 6 simultaneously to this movement. Generally, the beam detector 1 as well as the beam source 2 can be moved about at least two axes, wherein these movements can be linear movements as well as rotation movements and infinite combinations. In some embodiments, the two axes here are perpendicular to one another, but also, in further embodiment examples, infinite geometric arrangements of the two axes to one another can be used.

The X-ray source 2 likewise moves on a polynomial path 27 which, since the X-ray source 2 and the X-ray detector 1 lie opposite one another during their movement, likewise has a starting point 28 and an end point 29 which is spatially offset to this starting point 28, along a longitudinal axis of the operating table 6 thus a longest axis of the operating table 6. A reversal point 30 is located opposite these points 28 and 29 on the other side of the operating table 30.

The longitudinal displacement has its minimal or maximal deflection on a stretch between the starting point 24 and the first middle point 34 or between the second middle point 35 and an end point 25 of the path 23 of the X-ray detector 1. In some embodiments, the deflection can be designed in a variable manner on these sections, so that the deflection on a section between the starting point 24 and the reversal point 26 or between the reversal point 26 and the end point 25 is continuously increased for example.

In some embodiments, shown in FIG. 6, the deflection of the X-ray detector 1 is continuously changed on a stretch between the first middle point and the reversal point 26 or between the reversal point 26 and the second middle point. For this, the deflection is changed according to the mathematical function $d=0.5*d_{max}*\cos(\alpha_i(0.5*\alpha))$ wherein $\alpha_i$ corresponds to the current angular position of the X-ray source 2 on its movement path 27 with the opening angle $\alpha$ and $d_{max}$ characterizing the maximal deflection. Further courses are however also possible. Thus the movement path 23 can be defined by a mathematic function in Cartesian coordinates, cylinder coordinates or sphere coordinates, not only on the mentioned sections, but also on a complete stretch (section) between the starting point 24 and the reversal point 26 and/or on a complete stretch between the reversal point 26 and the end point 25.

In FIG. 6, the X-ray source is inclined in the opposite direction about the opening angle $\beta$ in dependence on the longitudinal displacement d of the X-ray detector 1, so that the central beam is always directed onto the X-ray detector 1. The inclination $\beta$ is computed according to the detector deflection, in a manner such that a beamed sensor surface of the X-ray detector 1 becomes maximal with a fixed cone beam opening angle $\gamma$. The inclination hereby corresponds to a maximal angle between a first middle position 36 and a second middle position 37 of the path 27. The middle positions 36, 37 of the path 27 hereby lie directly opposite the middle positions 34, 35 of the path 23. Alternatively or additionally, a complete imaging of a predefined volume size on the sensor surface can be a condition for the computation of the inclination $\beta$. Thus the inclination $\beta$ of the X-ray source 2 is maximal in the middle positions 34, 35 of the path 23, in the embodiment example shown in FIG. 6. The distance can also be adapted by way of the inclination $\beta$ as already described, i.e. a constant distance between the X-ray source 2 and the X-ray detector 1 for example can be set at each position, in which a projection recording is made.

That which has been stated with regard to the path of the X-ray detector 1 applies in the same manner to the path 27 of the X-ray source 2.

Figure 7:
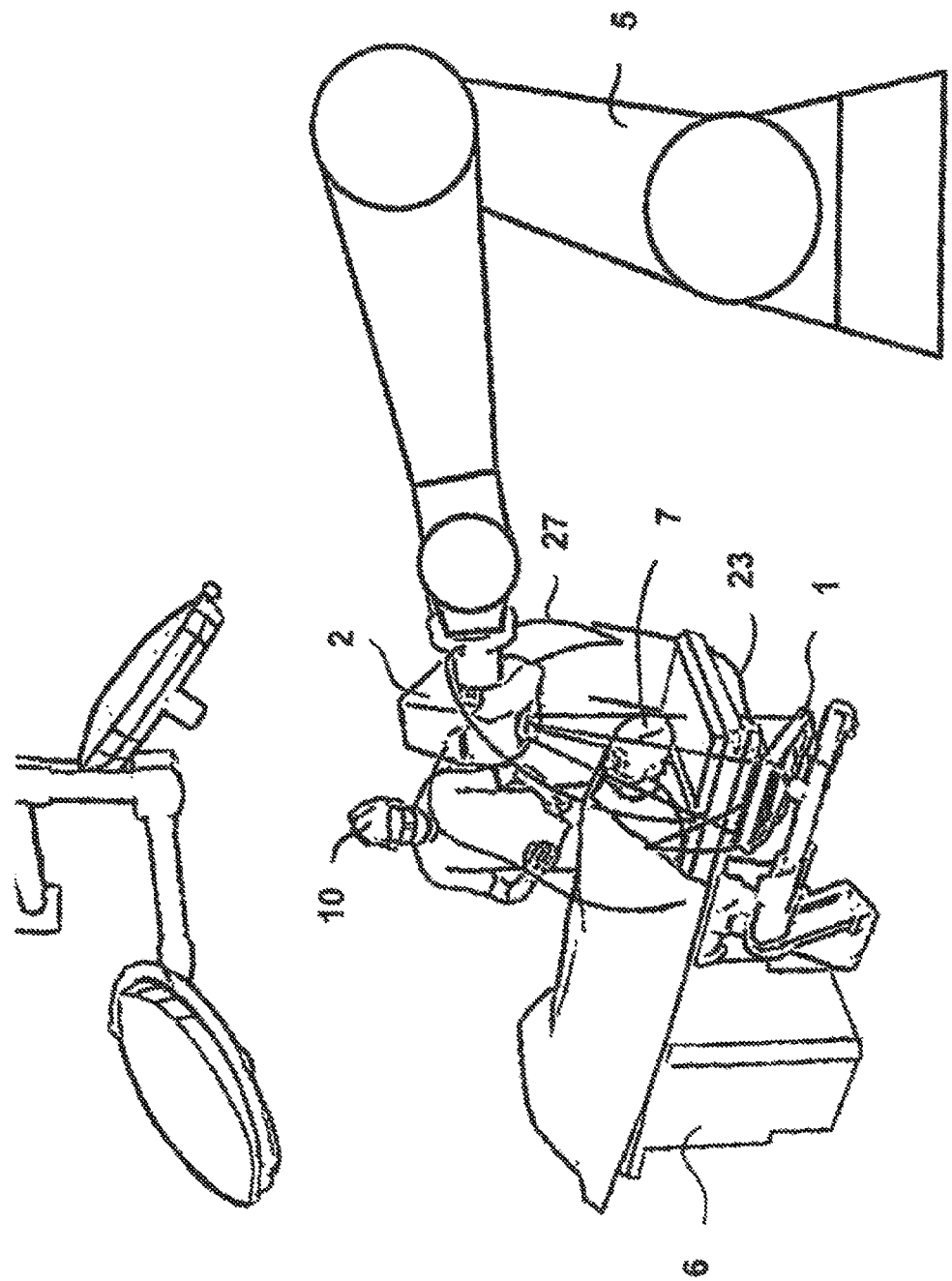
FIG. 7 a representation of the device with the movement paths, in a manner corresponding to FIG. 1, according to embodiments described in the disclosure.

FIG. 7 in a perspective view corresponding to FIG. 1 represents the movement paths 23 and 27 together with the robot arm, 5, the patient 7 and the X-ray detector 1. The movement paths 23 and 27 are likewise reproduced in FIG. 8 in representation corresponding to FIG. 2.

Figure 8:
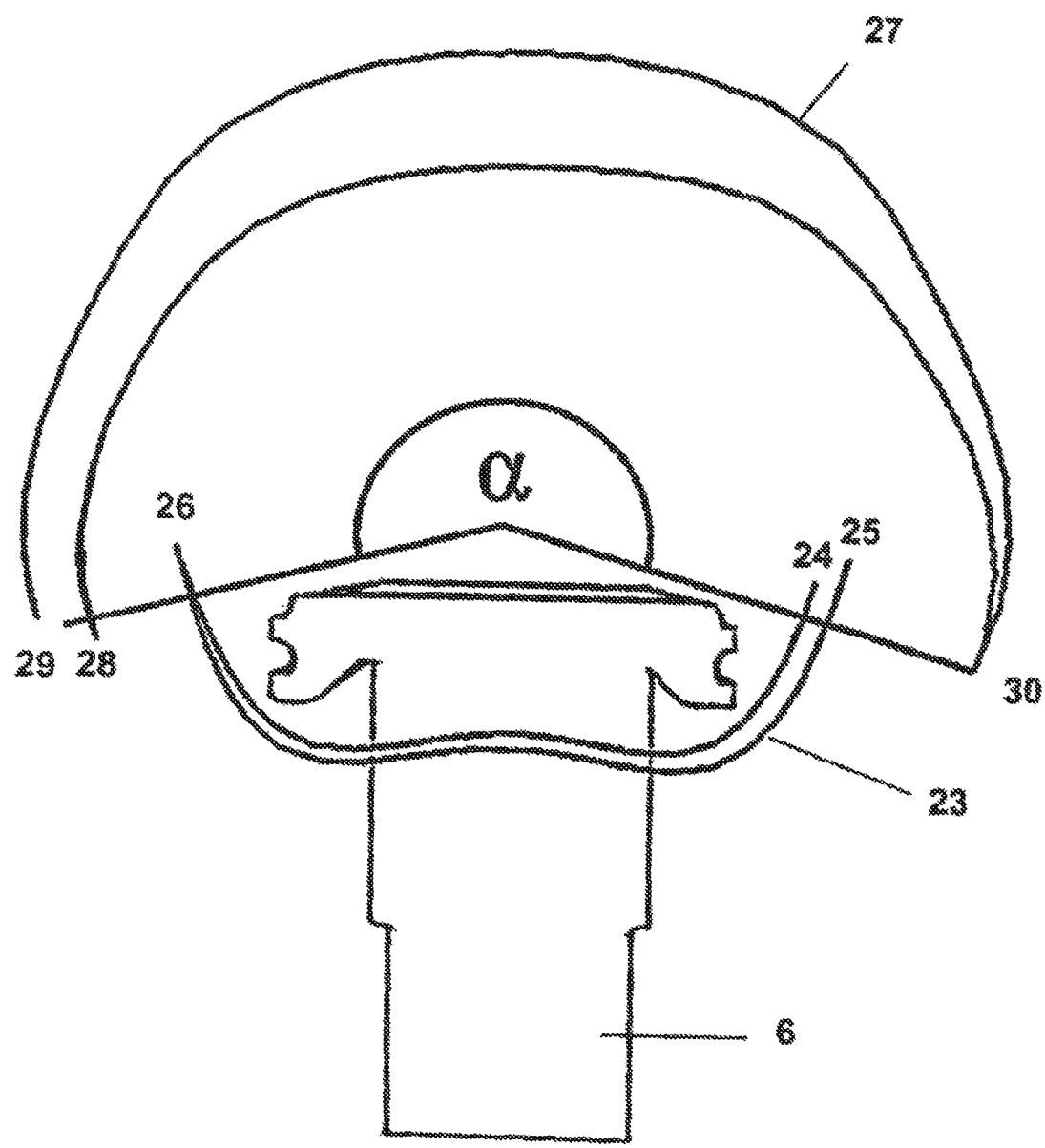
FIG. 8 a representation of embodiments of the movement paths with reversal points, in a manner corresponding to FIG. 2, according to embodiments described in the disclosure.
Figure 9:
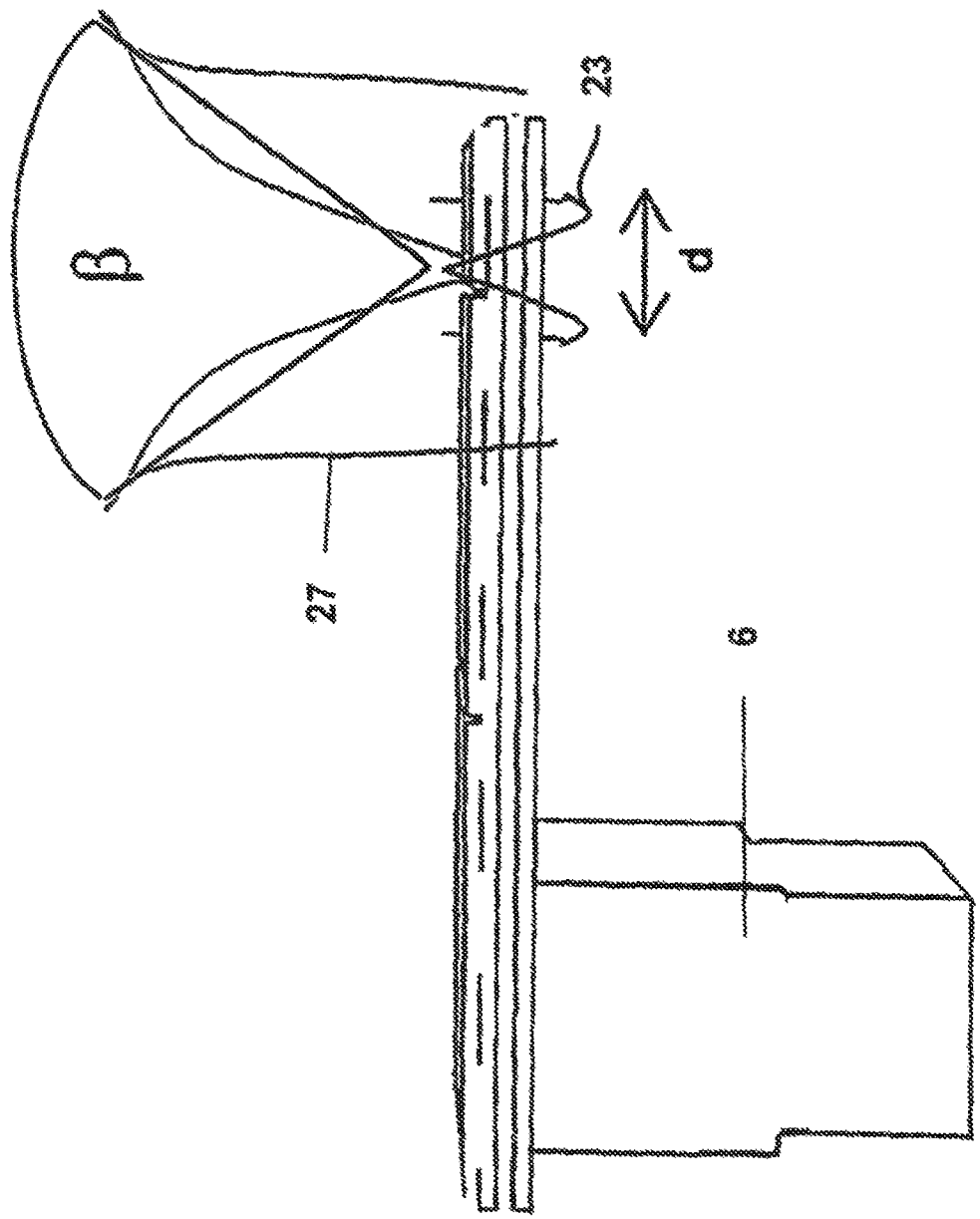
FIG. 9 a lateral view of the operating table with the movement paths which are represented in FIG. 8, according to embodiments described in the disclosure.
Figure 10:
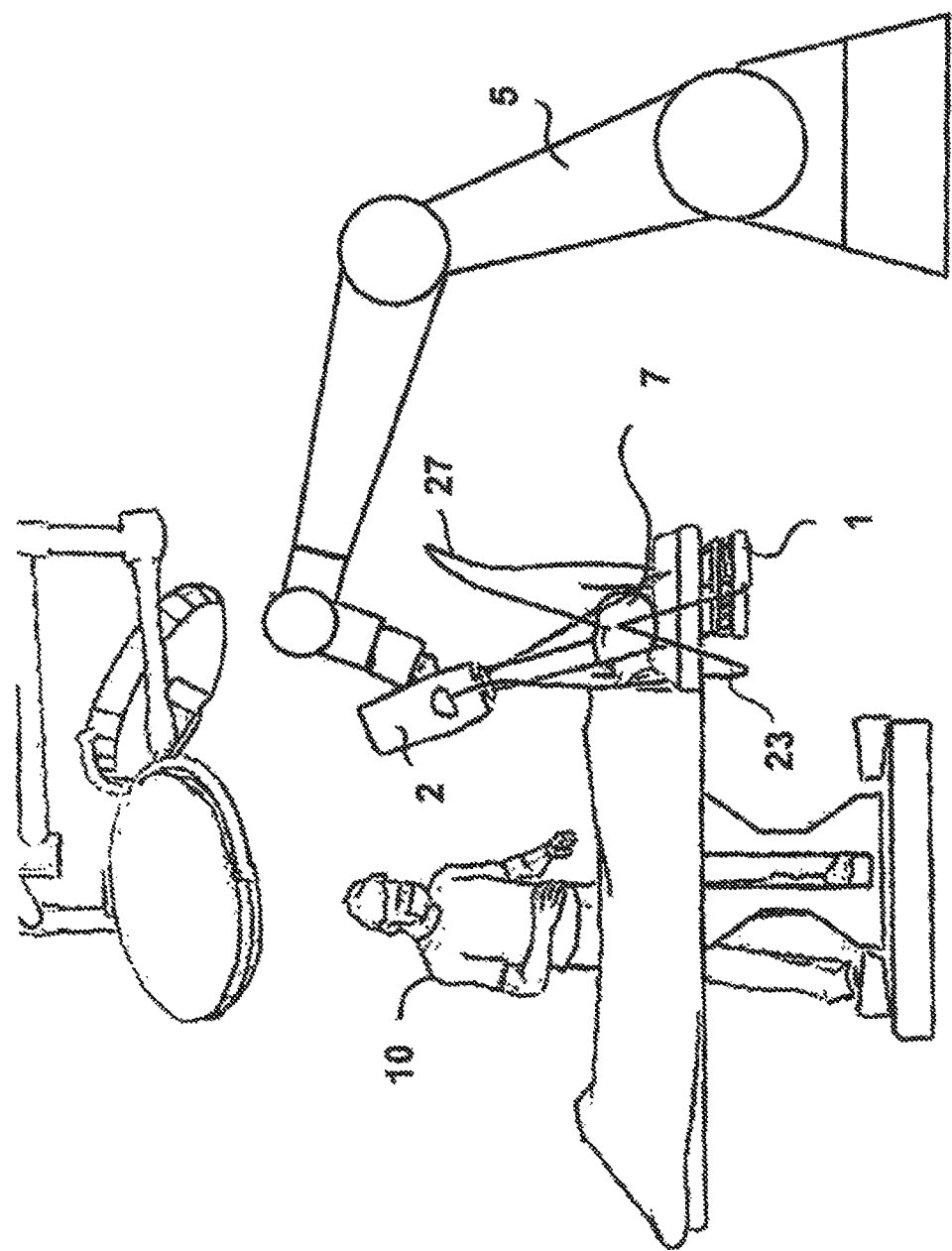
FIG. 10 a lateral view of the device with the movement paths represented in FIGS. 8 and 9, according to embodiments described in the disclosure.

A lateral view of FIG. 8 is shown in FIG. 9, from which the displacement in the longitudinal direction of the path 23 of the X-ray detector 1 as well as the inclination $\beta$ of the X-ray source together with its path 27 can be deduced. FIG. 10 in a lateral view of the device with the movement paths shown in FIGS. 8 and 9 shows how the X-ray source 2 is can be moved and inclined on its path by way of the robot arm 5. Moreover, the path 23 of the X-ray detector 1 is drawn. The paths 23 and 27 are open, thus each have a starting point and an end point which are not the same, and these paths do not completely enclose the patient 7.

In further embodiment examples, one of the movement paths of the X-ray source 2 and of the X-ray detector 1 or also both movement paths can be rowed or linked together several times. In this case, several reversal points are used between the respective starting points and end points.

The complete picture recording path or the both picture recording paths alternatively or additionally can be rotated about the target volume or the patient 7 and the operating table 6.

Figure 11:
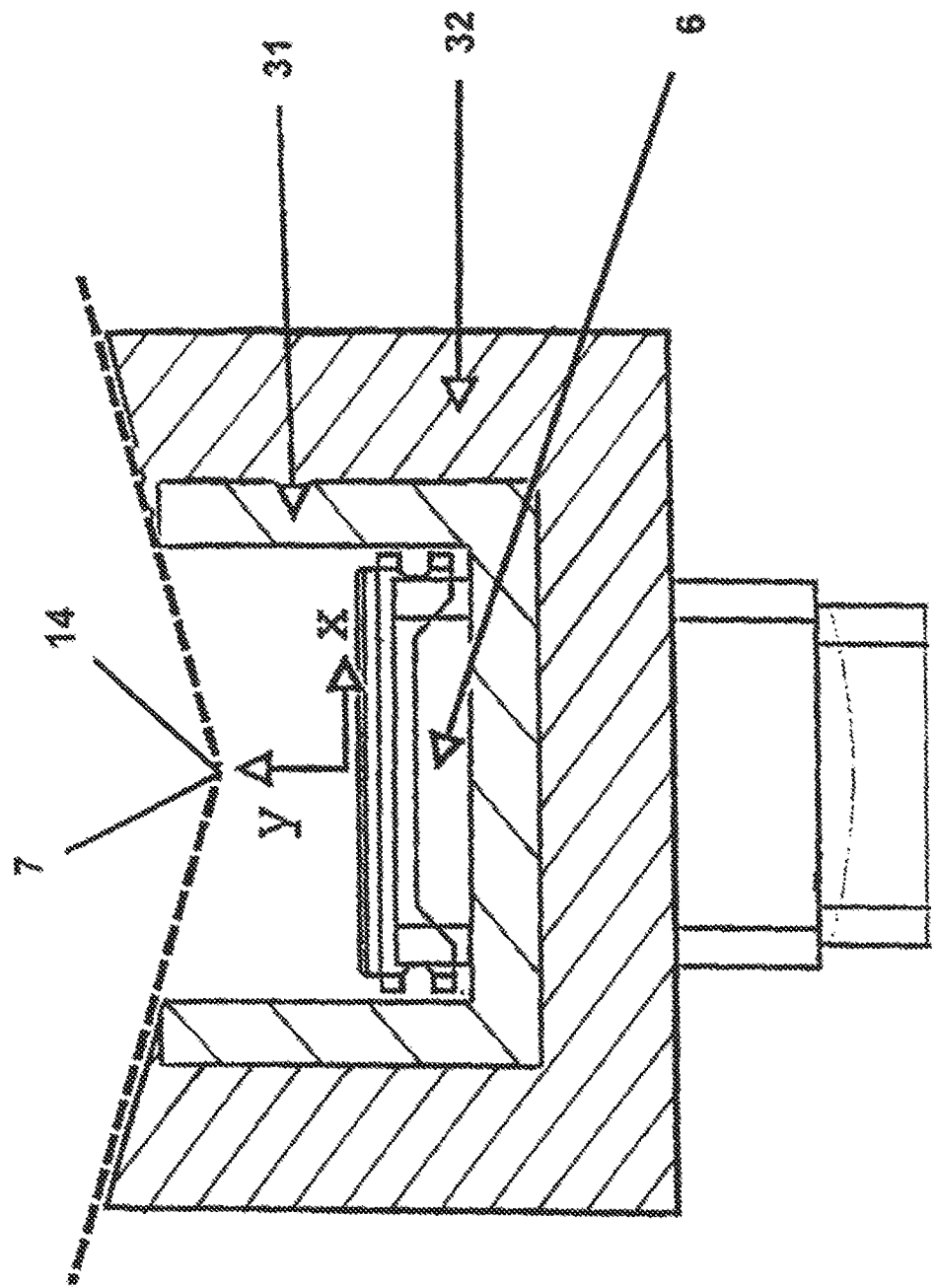
FIG. 11 a sectioned representation of the operating table with safety distances drawn in, according to embodiments described in the disclosure.

FIG. 11 shows a sectioned view of the operating table 6, with which a box-like safety region 31 which is taken into account on determining the polynomial displacement, is drawn around the patient 7. As a condition, one applies the fact that a housing of the X-ray source 2 and/or of the X-ray detector 1 must always be at least 80 mm from the operating table 6 and from the patient 7. A working region 32 as a further condition for the polynomial movement path of the X-ray detector 1 is also specified. This working region 32 takes into account a maximal distance to the patient 7 and/or a working region of kinematics for moving the X-ray detector 1. The working region 32 hereby describes the positions laterally and below the operating table 6, into which the X-ray detector 1 can be moved.

Figure 12:
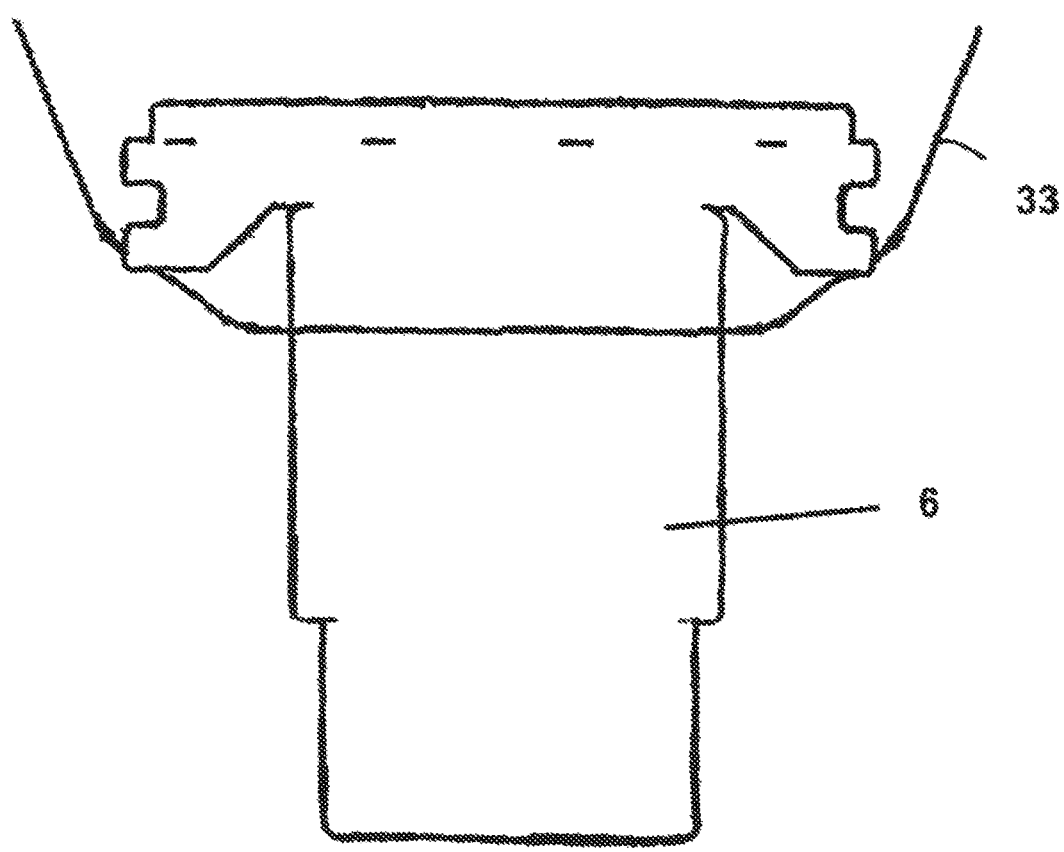
FIG. 12 a view of the operating table corresponding to FIG. 2, with embodiments of an initial movement path of the X-ray detector, according to embodiments described in the disclosure.

FIG. 12 finally in a representation corresponding to FIG. 2 represents a further possibility of an initial path 33 for the optimisation of the path of the X-ray detector 1. A path 33 consisting of individual linear sections is used instead of an arched path. A middle section below the operating table 6 runs parallel to a surface of the operating table 6. Angled, again linear running part-stretches are used subsequently to this middle part, for the completion of the path.

Features of the various embodiments and which have only been disclosed in the embodiment examples can be combined with one another and claimed individually.

LIST OF REFERENCE NUMERALS

1 X-ray detector
2 X-ray source
3 control unit
4 evaluation unit
5 robot arm
6 operating table
7 patient
8 cable
9 cable
10 user
11 screen
12 path
13 polynomial path
14 middle point
15 starting position
16 middle position
17 end position
18 polynomial path
19 central beam
20 central beam
21 end point
22 starting point
23 polynomial path
24 starting point
25 end point
26 reversal point
27 polynomial path
28 starting point
29 end point
30 reversal point
31 safety region
32 working region
33 path
34 middle position
35 middle position
36 middle position
37 middle position
38 cable

The invention claimed is:

1. A method for recording projection pictures of an object to be imaged by way of an imaging device that comprises an x-ray beam source, an x-ray beam detector, and a control unit, the method comprising:
   moving the x-ray beam source by the control unit on a path into several positions, in which in each of the several positions an x-ray beam departing from the x-ray beam source is emitted in a cone-beam-shape about a central x-ray beam;
   moving the x-ray beam detector, with the displacement of the x-ray beam source, by the control unit into several positions, in which in each of the several positions the x-ray beam which departs from the x-ray beam source and penetrates the object to be imaged is captured for recording a projection picture;
   wherein at least one of the x-ray beam source and the x-ray beam detector are displaced on a path about the object to be imaged, the path being described by a polynomial of the nth degree and computed by the control unit by way of an optimization of a predefined path, and with a variable distance between the x-ray beam source and a surface of the object to be imaged provided by the optimization of the predefined path, the distance determined along the central x-ray beam, wherein the polynomial is selected such that a safety distance to the object to be imaged is maintained and, simultaneously, a distance between the x-ray beam detector and the object to be imaged is minimized.

2. The method according to claim 1, wherein the polynomial is defined by at least two grid points and is determined by way of at least one of an optimization while taking into account the grid points and an optimization of a predefined circular path.

3. The method according to claim 1, wherein a maximal height of the path of the x-ray beam detector is determined by a maximal opening angle ($\alpha$) of the path of the x-ray beam source, the opening angle being determined by departing from a middle point of the object to be imaged, and wherein a starting point and an end point of the path of the x-ray beam detector lies opposite a starting point and an end point of the path of the x-ray beam source along the central x-ray beam running through the middle point of the object to be imaged.

4. The method according to claim 1, wherein the path of the movement of at least one of the x-ray beam source and the x-ray beam detector is at least one of:
   an open path that is open such that the open path does not completely enclose the object to be imaged; and
   a reversal point path that has at least one reversal point, in which a direction change takes place, and wherein a first path section up to the reversal point is spatially different to a second path section from the reversal point.

5. The method according to claim 1, wherein at least one of the x-ray beam detector and the x-ray beam source is moved in relation to at least two axes which are perpendicular to one another.

6. The method according to claim 1, wherein an inclination ($\beta$) of the x-ray beam source is set such that a beamed surface of the x-ray beam detector is maximized at a fixed angle of the cone beam.

7. The method according to claim 1, wherein at least one of the movements of the x-ray beam source and of the x-ray beam detector is carried out in an automated manner by way of the control unit.

8. The method according to claim 1, wherein an evaluation unit computes a three-dimensional reconstruction of the object to be imaged, from the projection pictures.

9. A computer program product stored on a non-transitory machine-readable medium and executed on a computation unit, the computer program product comprising a command sequence for carrying out the method according to claim 1, when executed on the computation unit.

10. A device for recording projection pictures of an object to be imaged, the device comprising:

an x-ray beam source configured to emit x-ray radiation in a cone-beam-shape about a central x-ray beam;

an x-ray beam detector configured to capture emitted x-ray radiation penetrating the object to be imaged; and a control unit configured to move the x-ray beam detector and the x-ray beam source into several positions and to record a projection picture in each of the several positions, wherein the control unit is configured to move the x-ray beam source and the x-ray beam detector on a path about the object to be imaged, the path being described by a polynomial of the nth degree and computed by the control unit by way of an optimization of a predefined path, and with a variable distance between the x-ray beam source and a surface of the object to be imaged provided by the optimization of the predefined path, the distance determined along the central x-ray beam, wherein the polynomial in each case is selected such that a safety distance to the object to be imaged is maintained and, simultaneously, a distance between the x-ray beam detector and the object to be imaged is minimized.

* * * * *